United States Patent [19]

Pease et al.

[11] Patent Number: 4,891,324
[45] Date of Patent: Jan. 2, 1990

[54] PARTICLE WITH LUMINESCER FOR ASSAYS

[75] Inventors: John Pease, Los Altos; Litai Weng, Mountain View; Hrair Kirakossian, San Jose; Edwin F. Ullman, Atherton, all of Calif.

[73] Assignee: Syntex (U.S.A.) Inc., Palo Alto, Calif.

[21] Appl. No.: 925

[22] Filed: Jan. 7, 1987

[51] Int. Cl.$^4$ .......................................... G01N 33/533
[52] U.S. Cl. ..................................... 436/519; 436/520; 436/522; 436/528; 436/533; 436/534; 436/535; 436/546; 436/800; 436/805; 436/808; 436/809; 436/821; 436/823; 436/829; 428/402
[58] Field of Search ............... 436/519, 520, 522, 528, 436/533, 534, 535, 546, 800, 805, 808, 809, 821, 823, 829; 427/2; 428/402

[56] References Cited

U.S. PATENT DOCUMENTS

| | | | |
|---|---|---|---|
| 3,850,578 | 11/1974 | McConnell | 436/829 |
| 4,311,712 | 1/1982 | Evans et al. | 436/829 |
| 4,372,745 | 2/1983 | Mandle | 436/537 |
| 4,373,932 | 2/1983 | Gribnau | 436/501 |
| 4,483,921 | 11/1984 | Cole | 435/7 |
| 4,483,929 | 11/1984 | Szoka | 436/533 |
| 4,485,054 | 11/1984 | Mezei et al. | 436/829 |
| 4,522,803 | 6/1985 | Lenk et al. | 424/1.1 |
| 4,529,561 | 7/1985 | Hunt et al. | 436/829 |
| 4,576,912 | 3/1986 | Yaverbaum et al. | 435/7 |
| 4,588,578 | 5/1986 | Fountain et al. | 424/1.1 |
| 4,605,630 | 8/1986 | Kung et al. | 436/511 |
| 4,628,037 | 12/1986 | Chagnon et al. | 436/526 |
| 4,698,263 | 10/1987 | Wagner | 436/546 |
| 4,748,129 | 5/1988 | Chang | 436/519 |

FOREIGN PATENT DOCUMENTS 2021262A 11/1979 United Kingdom .

OTHER PUBLICATIONS

Thorpe: Biochemical and Biophysical Research Communications, 119(2), 481–487, (1984).
Wilkins: Nature 202 (4937), 798–799 (1964).
Cram et al, "Organic Chemistry", 2nd Edition, p. 552, McGraw-Hill Book Co., New York.
Fieser & Fieser, "Advanced Organic Chemistry", (1961), pp. 370–380; 441–442; and 518–520, Reinhold Publishing Co., N.Y.
Kosolapoff, "Organophosphorus Compounds", pp. 232–233, John Wiley & Sons, New York.
Migrdichian, "Organic Synthesis", vol. 1, pp. 331–332, Reinhold Publishing Corp., New York.
O'Connell et al., Clin. Chem. 31 (9), 1424–1426 (1985).

*Primary Examiner*—Robert Benson
*Attorney, Agent, or Firm*—Theodore J. Leitereg; Carole F. Barrett; Gerald F. Swiss

[57] ABSTRACT

Assay methods are provided for determining an analyte in a sample suspected of containing the analyte. The method is carried out using a composition that includes a conjugate of a first sbp member with a particle. A luminescer is reversibly associated with a nonaqueous phase of the particle. Where the first sbp member is not complementary to the analyte, a second sbp member that is capable of binding to the first sbp member is employed. Unbound conjugate is separated from conjugate that is bound to the analyte or to the second sbp member. A reagent for enhancing the detectability of the luminescer is added and the light emission of the luminescer acted on by the reagent is measured.

56 Claims, No Drawings

PARTICLE WITH LUMINESCER FOR ASSAYS

BACKGROUND OF THE INVENTION

1. Field of the Invention

This invention relates to methods for performing an assay for determining an analyte by use of a conjugate of a member of a specific binding pair consisting of ligands and receptors, for example, antigens and antibodies, with a particle. The method of the invention has particular application to heterogeneous immunoassays of biological fluids, for example, serum or urine.

Luminescent compounds, such as fluorescent compounds and chemiluminescent compounds, find wide application because of their ability to emit light. For this reason, luminescers have been utilized as labels in assays such as immunoassays. For example, a member of a specific binding pair is conjugated to a luminescer and various protocols are employed. For example, the luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then adminstered to the patient to be treated.

Particles, such as latex beads and liposomes, have also been utilized in assays. For example, in homogeneous assays an enzyme may be entrapped in the aqueous phase of a liposome labelled with an antibody or antigen. The particles are caused to release the enzyme in the presence of a sample and complement. Antibody or antigen-labelled particles, such as liposomes, having water soluble fluorescent or non-fluorescent dyes encapsulated within an aqueous phase of the lipid vesicle, have also been utilized to assay for analytes capable of entering into an immunochemical reaction with the surface bound antibody or antigen. Detergents have been used to release the dyes from the aqueous phase of the liposomes.

In cases in which the dye is incorporated within the aqueous layer of the particle, vesicle leakage is a problem. Fluorescent dyes incorporated in the aqueous layer have been observed to spill out as a result of some secondary effect of antigen-antibody binding. In addition, homogeneous methods involve no separation, and therefore, are subject to interferences from the sample.

It is, therefore, desirable to develop a new heterogeneous assay method, which has the ease and convenience of a homogeneous method, for determining an analyte in a sample. Additionally, it is also desirable to provide a sensitive heterogeneous immunoassay which provide amplification of the signal by releasing many detectable molecules per binding event without utilizing enzyme labels which require temperature and time controlled reactions. Direct labelling with luminescers, radio labels and the like, do not provide such an immunoassay. Such a sensitive immunoassay method, which is more fully described below, utilizes a conjugate of a specific binding pair member with a particle bearing a multiplicity of luminescer molecules. The luminescer is reversibly associated with a nonaqueous layer of the particle and can be released of the dye into solution during the assay to provide more sensitive determinations of the amount of analyte in the sample.

2. Description of the Related Art

O'Connell, et al., *Clin. Chem.*, (1985) 31(9), 1424–1426 discloses a colorimetric immunoassay for digoxin utilizing large, unilamellar phospholipid vesicles having dye entrapped in the aqueous phase of the liposome. U.S. Pat. Nos. 3,850,578; 4,483,921; and 4,483,929 disclose immunoreactive liposome reagents in which antigen or antibody is bound to the surface of lipid vesicles. U.S. Pat. Nos. 4,529,561; 4,522,803; and 4,485,054 disclose a variety of methods for preparing lipid vesicles. U.S. Pat. No. 4,311,712 discloses a process for preparing a freeze dried liposome mixture. U.S. Pat. No. 4,588,578 discloses a method for the preparation of monophasic lipid vesicles and the use of such vesicles for drug delivery systems. U.S. Pat. No. 4,576,912 discloses a method of enhancing the fluorescent level of an immunoassay using certain long-chain carriers tagged with a plurality of fluorophores.

SUMMARY OF THE INVENTION

Methods are provided for determining the presence of an analyte that is a member of a specific binding pair (sbp)—ligand and its complementary receptor—in a sample suspected of containing the analyte. The method is carried out using a composition that includes a conjugate of a first sbp member with a particle. A luminescer is reversibly associated with a nonaqueous phase of the particle. Where the first sbp member is not complementary to the analyte, a second sbp member that is capable of binding to the analyte and to the first sbp member is employed. The particle can be a synthetic or natural vehicle. The luminescer can be a fluorescer or a chemiluminescer. The unbound conjugate is separated from the conjugate that is bound to the analyte or to the second sbp member. A reagent for enhancing the detectability of the luminescer is added to the bound or to the unbound conjugate and the light emission of the luminescer acted on by the reagent is measured.

The method of the present invention has particular application in an assay for organic and biochemical analytes particularly where a labelled particle is employed. Analytes of interest in the analysis of body fluids include, drugs, such as theophylline, thyroxine and digoxin, proteins, polypeptides, nucleic acids and polysaccharides.

Of special interest are assays where a second sbp member is bound to a solid support. In such an assay binding between the first and the second sbp members is affected by the concentration of the analyte in the sample. Where a second sbp member bound to a solid support is utilized, the method involves combining in an assay medium the sample, a conjugate of the first sbp member and a particle with a luminescer reversibly associated with the nonaqueous phase of the particle, and the second sbp member bound to a support. The support is separated from the medium and then a reagent is added to enhance the detectability of the luminescer. Thereafter, the light emission of the luminescer in combination with the reagent is measured.

The invention includes kits for conducting the method of the invention, particularly for conducting an assay for determining an analyte in a sample suspected of containing the analyte. A reagent for enhancing the detectability of the luminescer and ancillary reagents can also be provided in the kits.

DESCRIPTION OF THE SPECIFIC EMBODIMENTS

The present invention relates to the detection of luminescence as a measure of an analyte in a sample suspected of containing such analyte where the method involves enhancing luminescence. The method of the present invention involves reversibly associating a luminescer with a nonaqueous phase of a particle conjugated to a member of a specific binding pair and enhancing the detectability of the luminescer at a prescribed time. The luminescer is present in the nonaqueous phase of the particle. A sensitive, accurate heterogeneous assay method is provided utilizing the above particle conjugate for determining a wide variety of analytes in a sample suspected of containing the analyte. Luminescers utilized in the present invention include chemiluminescers and fluorescers.

In accordance with the subject invention, an assay method is provided for determining the presence of an analyte that is a member of a specific binding pair (sbp) consisting of ligand and its complementary receptor. The sample suspected of containing the analyte is combined with a composition that includes a conjugate of a first sbp member with a particle having a luminescer reversibly associated with a nonaqueous phase of the particle. Where the first sbp member is not complementary to the analyte, a second sbp member is added to the medium. The second sbp member is capable of binding to the analyte and to the first sbp member. The unbound conjugate is separated from the conjugate that is bound to the analyte or to the second sbp member, and a reagent for enhancing the detectability of the luminescer is added to the bound conjugate or to the unbound conjugate. The light emitted by the luminescer that has been acted upon by the reagent is measured.

Before proceeding further with the description of specific embodiments of the present invention, a number of terms will be defined.

Analyte—the compound or composition to be measured, the material of interest. The analyte can be a member of a specific binding pair (sbp) and may be a ligand, which is mono- or polyvalent, usually antigenic or haptenic, and is a single compound or plurality of compounds which share at least one common epitopic or determinant site.

The polyvalent ligand analytes will normally be poly(amino acids), i.e., polypeptides and proteins, polysaccharides, nucleic acids, and combinations thereof. Such combinations include components of bacteria, viruses, chromosomes, genes, mitochondria, nuclei, cell membranes and the like.

The precise nature of some of the analytes together with numerous examples thereof are disclosed in U.S. Pat. No. 4,299,916 to Litman, et al., particularly at columns 16 to 23, the disclosure of which is incorporated herein by reference.

For the most part, the polyepitopic ligand analytes employed in the subject invention will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc.

The monoepitopic ligand analytes will generally be from about 100 to 2,000 molecular weight, more usually from 125 to 1,000 molecular weight. The analytes of interest include drugs, metabolites, pesticides, pollutants, and the like. Included among drugs of interest are the alkaloids. Among the alkaloids are morphine alkaloids, which include morphine, codeine, heroin, dextromethorphan, their derivatives and metabolites; cocaine alkaloids, which include cocaine and benzoyl ecgonine, their derivatives and metabolites, ergot alkaloids, which include the diethylamide of lysergic acid; steroid alkaloids; iminazoyl alkaloids; quinazoline alkaloids, isoquinoline alkaloids; quinoline alkaloids, which include quinine and quinidine; diterpene alkaloids, their derivatives and metabolites.

The next group of drugs includes steroids, which includes the estrogens, estogens, androgens, andreocortical steroids, bile acids, cardiotonic glycosides and aglycones, which includes digoxin and digoxigenin, saponins and sapogenins, their derivatives and metabolites. Also included are the steroid mimetic substances, such as diethylstilbestrol.

The next group of drugs is lactams having from 5 to 6 annular members, which include the barbituates, e.g. phenobarbital and secobarbital, diphenylhydantonin, primidone, ethosuximide, and their metabolites.

The next group of drugs is aminoalkylbenzenes, with alkyl of from 2 to 3 carbon atoms, which includes the amphetamines, catecholamines, which includes ephedrine, L-dopa, epinephrine, narceine, papaverine, and their metabolites.

The next group of drugs is benzheterocyclics which include oxazepam, chlorpromazine, tegretol, imipramine, their derivatives and metabolites, the heterocyclic rings being azepines, diazepines and phenothiazines.

The next group of drugs is purines, which includes theophylline, caffeine, their metabolites and derivatives.

The next group of drugs includes those derived from marijuana, which includes cannabinol and tetrahydrocannabinol.

The next group of drugs includes the vitamins such as A, B, e.g. $B_{12}$, C, D, E and K, folic acid, and thiamine.

The next group of drugs is prostaglandins, which differ by the degree and sites of hydroxylation and unsaturation.

The next group of drugs is antibiotics, which include penicillin, chloromycetin, actinomycetin, tetracycline, terramycin, the metabolites and derivatives.

The next group of drugs is the nucleosides and nucleotides, which include ATP, NAD, FMN, adenosine, guanosine, thymidine, and cytidine with their appropriate sugar and phosphate substituents.

The next group of drugs is miscellaneous individual drugs which include methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, their metabolites and derivatives.

Metabolites related to diseased states include spermine, galactose, phenylpyruvic acid, and porphyrin Type 1.

The next group of drugs is aminoglycosides, such as gentamicin, kanamicin, tobramycin, and amikacin.

Among pesticides of interest are polyhalogenated biphenyls, phosphate esters, thiophosphates, carbamates, polyhalogenated sulfonamides, their metabolites and derivatives.

For receptor analytes, the molecular weights will generally range from 10,000 to $2 \times 10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may be $10^6$ or higher molecular weight, including such materials as avidin, DNA, RNA, thyroxine binding globulin, thyroxine binding prealbumin, transcortin, etc.

Ligand analog or analyte analog—a modified ligand or ligand surrogate or modified analyte or analyte surrogate which can compete with the analogous ligand or analyte for a receptor, the modification providing means to join a ligand analog or analyte analog to another molecule. The ligand analog or analyte analog will usually differ from the ligand or analyte by more than replacement of a hydrogen with a bond which links the ligand analog or analyte analog to a hub or label, but need not. The term ligand surrogate or analyte surrogate refers to a compound having the capability of specifically binding a receptor complementary to the ligand or analyte. Thus, the ligand surrogate or analyte surrogate can bind to the receptor in a manner similar to the ligand or analyte. The surrogate could be, for example, an antibody directed against the idiotype of an antibody to the ligand or analyte.

Poly(ligand analog)—a plurality of ligand analogs joined together covalently, normally to a hub nucleus. The hub nucleus is a polyfunctional material, normally polymeric, usually having a plurality of functional groups, e.g., hydroxyl, amino, mercapto, ethylenic, etc. as sites for linking. The hub nucleus may be water soluble or insoluble, preferably water soluble, and will normally be at least about 30,000 molecular weight and may be 10 million or more molecular weight. Illustrative hub nuclei include polysaccharides, polypeptides (including proteins), nucleic acids, anion exchange resins, and the like. Water insoluble hub nuclei can also include walls of containers, e.g. glass or plastic, glass beads, addition and condensation polymers, Sephadex and Agarose beads and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, DNA-DNA, DNA-RNA, and the like are not immunological pairs but are included in the invention.

Ligand—any organic compound for which a receptor naturally exists or can be prepared.

Receptor (antiligand)—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids and the like.

Support or surface—a porous or non-porous water insoluble material. The surface can be hydrophilic or capable of being rendered hydrophilic and can be formed from inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass, ceramics, metals, and the like.

Binding of sbp members to the surface may be accomplished by well-known techniques, commonly available in the literature. See, for example, "Immobilized Enzymes," Ichiro Chibata, Halsted Press, NY (1978) and Cautrecasas, *J. Biol. Chem.*, 245:3059 (1970).

Particles—particles of at least about 20 nm and not more than about 20 microns, usually at least about 40 nm and less than about 10 microns, preferably from about 0.10 to 2.0 microns diameter. The particle may be organic or inorganic, swellable or non-swellable, porous or non-porous, preferably of a density approximating water, generally from about 0.7 to about 1.5 g/ml, and composed of material that can be transparent, partially transparent, or opaque. The particles may or may not have a charge, and when they are charged, they are preferably negative. The particles will generally be latex particles, but can also include particles comprised of organic or inorganic polymers, preferably liposomes, phospholipid vesicles and oil droplets. The particles may also be cells, but because of the difficulty of obtaining reproducible and stable preparations, cells are not as desirable.

The organic particles will normally be polymers, either addition or condensation polymers, which are readily dispersible in the assay medium. The organic polymers will also be adsorptive or functionalizable so as to bind, either directly or indirectly, an sbp member.

The particles can be derived from naturally occuring materials, naturally occurring materials which are synthetically modified and synthetic materials. Natural or synthetic assemblies such as liposomes and phospholipid vesicles are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyvinyl alcohol, homopolymers and copolymers of derivatives of acrylate and methacrylate, particularly esters and amides having free hydroxyl functionalities, and the like. Inorganic polymers include silicones, glasses, available as Bioglas, and the like.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to a support or to an sbp member through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem.*, 245:3059 (1970). The length of a linking group may vary widely, depending upon the nature of the compound being linked, the effect of the distance between the compound being linked and the particle on the binding of sbp members and the analyte and the like.

Liposomes, which are microvesicles of approximately spherical shape are preferred for use in the present invention. The liposomes have a diameter that is at least about 20 nm not more than about 20 microns, usually at least about 40 nm and less than about 10 microns. Preferably the diameter of the liposomes will be less than about two (2) microns so as to limit settling.

The outer shell of a liposome consists of a phospholipid bilayer that encloses a volume of water or an aqueous solution. Liposomes with more than one bilayer are referred to as multilamellar vesicles. Liposomes with only one bilayer are called unilamellar vesicles. Multilamellar vesicles are preferred in the present invention because of their ability to incorporate larger quantities of dye than unilamellar vesicles. The phospholipids employed in preparing particles utilizable in the present invention can be any phospholipid or phospholipid mixture found in natural membranes including lecithin, or synthetic glyceryl phosphate diesters of saturated or unsaturated 12-carbon or 24-carbon linear fatty acids wherein the phosphate can be present as a monoester, or as an ester of a polar alcohol such as ethanolamine, choline, inositol, serine, glycerol and the like. Particularly preferred phospholipids include L-$\alpha$-palmitoyl oleoyl-phosphatidylcholine (POPC), palmitoyl oleoyl-phosphatidyl-glycerol (POPG), L-$\alpha$-dioleoylphosphatidylglycerol, L-$\alpha$-(dioleoyl)-phosphatidyl ethanolamine (DOPE) and L-$\alpha$(dioleoyl)-phosphatidyl $\beta$-(4-(N-maleimidomethyl)cyclohexane-1-carboxyamido)ethanol (DOPE-MCC).

The phospholipids in the bilayer may be supplemented with cholesterol and may be replaced with other amphiphilic compounds that have a polar head group, usually charged, and a hydrophobic portion usually comprised of two linear hydrocarbon chains. Examples of such subtitutes include diacylphosphate, dialkoxypropylphosphates wherein the alkyl groups have linear chains of 12-20 carbon atoms, N-(2,3-di(9-(Z)-octa-decenyloxy))-prop-1-yl-N,N,N-trimethyl ammonium chloride (DOTMA), as disclosed in U.S. patent application Ser. No. 811,146 filed on Dec. 19, 1985, which is hereby incorporated by reference herein, sphingomyelin, cardiolipin, and the like.

Liposomes utilized in the present invention preferably have a high negative charge density to stabilize the suspension and to prevent spontaneous aggregation.

For use in the present invention the liposomes must be capable of forming a conjugate with an sbp member and be capable of having a luminescer reversibly associated with the nonaqueous phase. The liposomes of the present invention are formed with sbp members conjugated to the outer surface of the lipid vesicle.

Liposomes may be produced by a variety of methods including hydration and mechanical dispersion of dried phospholipid or phospholipid substitute in an aqueous solution. Liposomes prepared in this manner have a variety of dimensions, compositions and behaviors. One method of reducing the heterogeneity and inconsistency of behavior of mechanically dispersed liposomes is by sonication. Such a method decreases the average liposome size. Alternatively, extrusion is useable as a final step during the production of the liposomes. U.S. Pat. No. 4,529,561 discloses a method of extruding liposomes under pressure through a uniform pore-size membrane to improve size uniformity.

Preparation of liposome dyed particles can be carried out in a variety of methods, including a method described by Olsen et al, *Biochemica et Biophysica Acta*, 557(9), 1979. Briefly, a mixture of lipids containing the appropriate dye is dried to a thin film on the walls of a glass vessel. The lipid film is hydrated in an appropriate buffer by shaking or vortexing. Thereafter, the lipid suspension is extruded through a series of polycarbonate filter membranes having successively smaller pore sizes.

A further illustrative method of preparing a liposome dyed particle involves combining the selected phospholipids and dye in a chloroform solution and then removing the chloroform under a stream of nitrogen. Remaining traces of solvent can be removed, for example, using high vacuum. Phosphate or other suitable solvent is added to the vessel containing the lipid film and vortexed until no residue can be detected. The crude lipid suspension is then extruded through a series of memberanes of successively smaller pore size. For example, 2.0 $\mu$, 1.0 $\mu$, 0.8 $\mu$, 0.6 $\mu$, 0.4 $\mu$, and 0.2 $\mu$. Repeated filtration through any of the filters, and in particular through the smallest filter, is desirable. The liposomes can be purified by, for example, gel filtration, such as through a column of Sephacryl S-1000. The column can be eluted with buffer and the liposomes collected. Storage in the cold prolongs shelf-life of the liposomes produced by this method. Availability of the maleimide function on the surface of the liposome vesicles is confirmable, for examples, by reaction with a known quantity of a sulfhydryl standard, such as cysteine. Excess sulfhydryl standard can be determined using Ellman's reagent, and thus, maleimide is determined by difference.

Sbp members can be attracted to the surface of the liposome particles by weak hydrophobic interactions, however such interactions are not generally sufficient to withstand the shear force encountered during incubation and washing. It is preferable to covalently bond sbp members to a liposome particle that has been functionalized, for example by use of DOPE-MCC, as shown above, by combining said liposome with the selected sbp member. For example, if the sbp member is monoclonal antibody against human thyroid stimulating hormone (hTSH), it may be reacted with S-acetyl-mercaptosuccinic anhydride (SAMSA) to provide a sulfhydryl modified antibody.

Latex particles are also particularly utilizable in the present invention. "Latex" signifies the residue of a water insoluble polymeric material containing carboxyl groups which is immunologically compatible with expected use conditions. The latex portion is preferably derived from ethylenically unsaturated polymers and especially from such polymers as: polystyrene-butadiene, polystyrene, polystyrene with amino groups, polyacrylic acid, polymethacrylic acid, acrylonitrile-butadiene, styrene copolymers, polyvinyl acetate-acrylate, polyvinyl pyridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

In carrying out the dyeing of latex particles utilized in the present invention, a liquid, usually aqueous medium will be employed. Frequently, cosolvents will be utilized, such as alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like. The use of solvents having high boiling points in which the particles are insoluble permits the use of elevated temperatures to facilitate dyeing of the particles and are particularly suitable. The solvents may be used singly or in combination.

Where a carboxylate modified latex is chosen as the particle, the particles will have a formal negative surface charge. It is preferable, therefore, to use electronically neutral dyes. It is preferable that the liquid medium selected does not soften the polymer beads to the point of stickiness. A preferred technique comprises suspending the selected latex particlles in a liquid medium in which the dye has at least limited solubility. Preferably, the liquid medium should be saturated with respect to the dye to ensure that a sufficient quantity of dye is associated with the particles. Distortion or dissolution of the particles in the solvent can be prevented by adding a miscible cosolvent in which the particles are insolvent.

Generally, the temperature employed during the dyeing procedure will be chosen to maximize the amount of dye incorporated by the particles. With the proviso that the particles should not melt or become aggregated at the selected temperature, elevated temperatures are normally employed for dyeing particles used in the present invention. The temperatures for the dyeing will generally range from 20° C. to 200° C., more usually from 50° C. to 170° C. It has been observed that dyes that are nearly insoluble at room temperature, are soluble in, for example, low molecular weight alcohols, such as ethanol and ethylene glycol and the like, at about 170° C. Carboxylated modified latex particles have been shown to tolerate low molecular weight alcohols at such temperatures.

In some cases, for example, where the particle selected is a polystyrene latex and the dye selected is a squarate dye, it may be necessary to control the solubility of the dye to ensure that the desired amount of dye is reversibly associated with the latex. For dyes not sufficiently soluble, a cosolvent, for example a low molecular weight alcohol, such as benzyl alcohol, ethanol and ethylene glycol, at concentrations up to about 25%, and preferably up to about 20% without damaging the particles. Carboxylated-modified latex is very tolerant of low molecular weight alcohols even at temperatures up to about 170° C. If a dye is very soluble in the solvent, it may be preferable to use concentrated solutions to get sufficient dye into the particles.

The concentration of luminescers reversibly associated with each particle should be sufficient to provide a larger signal than would be provided, if the luminescer were directly conjugated to an sbp member. Usually, the luminescer to sbp member ratio on the particles should be at least 10 to 1, preferably at least 100 to 1, and most preferably over 1,000 to 1.

The sbp member may be physically adsorbed on the surface of the dyed latex particle or may be covalently bonded to the particle. In cases wherein the sbp member is attracted to the surface of the latex particle by weak hydrophobic interactions and Van der Waal's forces, such attractions may in certain cases be unable to endure particle-to-particle shear forces encountered during incubation and washings. Therefore, it may be preferable to covalently bond sbp members to the latex particles under conditions that will minimize adsorption. One method to prevent adsorption is to coat the latex particle with a material that will prevent intimate contact of the latex surface and the sbp member. The material selected will preferably provide suitable functionality for both attachment to the latex particle and attachment of the sbp member. Suitable materials include maleimidated aminodextran ($MAD_x$), ethyl-3-(dimethylaminopropyl) carbodiimide hydrochloride (EDAC), and the like. $MAD_x$ can be prepared as described by Hubert et al, *Proc. Natl. Acad. Sci.*, 75(7), 3143, 1978.

In one method, $MAD_x$ is first attached to the latex particle using a water soluble carbodiimide, for example 1-(3-dimethylaminopropyl)-3-ethyl carbodiimide. The coated particle is then equilibrated in reagents to prevent nonspecific binding. Such reagents include protein, such as bovine gamma globulin (BGG), and detergent, such as Tween 20, TRITON X-100 and the like. The sbp member suitably modified to form a covalent bond to $MAD_x$ is then added to the mixture. The excess unreacted sbp member can then be removed by washing.

Label—A member of the signal producing system including any luminescer as defined herein.

Luminescer—The term luminescer is intended to include substances that emit visible or invisible radiation unaccompanied by high temperature as a result of chemical change or absorption of exciting energy in the form of photons or charged particles. Luminescers includes chemiluminescent substances and fluorescent substances, such as squarate dyes. The luminescers of interest will generally emit a wavelength above 400 nanometers and preferably above 500 nm.

Dyes that absorb and emit light at wavelengths beyond the region where serum components contribute to significant fluorescence will be of particular use in the present invention. The fluorescence of serum drops off rapidly above 500 nm and becomes insignificant above 600 nm; therefore, dyes that emit light above 600 nm are of particular interest. The 632.6 nm emission line of a helium-neon laser is an inexpensive light source for excitation. Dyes that adsorb light in the region of about 620 to about 650 nm are compatible with the emission line of a helium-neon laser and are, therefore, particularly useful in the present invention.

The reversibly associated luminescer will frequently be a fluorescer chosen from the group comprising squarate dyes, umbelliferones, fluoresceins, cyanines, merocyanines and rhodamines. A preferred luminescer is a squarate dye having an absorption maximum greater than 600 nm; preferably the maximum is 620 to 650 nm.

In those cases wherein the particle selected has a formal surface charge, for example, carboxylate modified latex (negative surface charge), it is preferable the dye selected not carry a formal charge, e.g. a coumarin dye. Such a dye passes more easily through the surface of charged particles than a dye which itself has formal charge.

The reversibly associated luminescer utilizable in the present invention is in some instances dissolved in the nonaqueous phase of the particle in such a manner that the luminescer is temporarily incapable of producing a signal. In one embodiment the dissolved luminescer is a squarate dye. The reversibly associated luminescer may also be non-covalently adsorbed at the surface of a nonaqueous phase of the particle. In one such embodiment the luminescer is bound to a polycation and is adsorbed on a liposome phospholipid membrane. In yet another embodiment the luminescer is a luminol derivative and the particle is a polystyrene latex bead. In another embodiment the luminescer is bound to the particle by chemically labile covalent bonds.

Squarate dye—a dye having the structural element of cyclobutenonolate, generally being a condensation product of squaric acid (dihydroxycyclobutenedione) and an active compound such as an indole or an aniline. The squarate dye utilizable in the present invention is preferably lipophilic and generally has an absorption maximum greater than 600 nanometers, and preferably has a maximum of 620 to 650 nm.

The molar extinction coefficient for the squarate dye at the wavelength of the exciting light should be as high as practical and should be greater than 10,000, preferably greater than 100,000 $M^{-1} cm^{-1}$. The squarate dyes should have a high quantum yield, normally greater than 0.05, preferably greater than 0.3.

Signal Producing System—The signal producing system may have one or more components, at least one component being a luminescer. The signal producing system generates a signal that relates to the presence or amount of analyte in a sample. The signal producing system includes all of the reagents required to produce a measurable signal including means for causing electronic excitation of the luminescer when a chemiluminescent substance is utilized. A preferred means of exciting fluorescence is a laser, for example, a He/Ne laser with an emission wave length at about 633 nm. However, other light sources can be employed, provided only that the wavelengths of the excitation are absorbed by the fluorescent substance. Other components of the signal producing system will usually be required when the luminescer is a chemiluminescent substance, including most commonly a source of hydrogen peroxide and in certain instances a base, organic solvent and/or catalyst such as ferrocyanide or iron porphyrin.

Ancillary Materials—Various ancillary materials will frequently be employed in an assay in accordance with the present invention. For example, buffers will normally be present in the assay medium, as well as stabilizers for the assay medium and the assay components. Frequently, in addition to these additives, additional proteins may be included, such as albumins, or surfactants, particularly non-ionic surfactants, binding enhancers, e.g., polyalkylene glycols, or the like.

Reagent for Enhancing Detectability—One or more reagents are utilized to increase the detectability of the luminescer that is associated with the nonaqueous phase of the particle. In some cases the ability of a luminescer dissolved in the nonaqueous phase of a particle or adsorbed on a nonaqueous phase of a particle to produce a signal is reduced. In such cases a reagent is employed for reversing the association between the particle and the luminescer. In other cases the luminescer can be bound to the particle by means of a chemical bond such as a covalent bond. In such cases a reagent is employed for reversing the association of the luminescer and the particle, e.g., by cleaving the bond between the luminescer and the particle or by otherwise enhancing the detectability of the signal.

Generally, any reagent including any chemical compound, composition, or material, either naturally occurring or synthetic, organic or inorganic, or any enzymatic method that is capable of enhancing the detectability of the luminescer and does not substantially interfere with the assay performance can be used in the present invention. The reagent selected for use in enhancing detectability of the luminescer in a particular assay will depend on such factors as the composition of the dye and the particle, and the nature of the association between the particle and the dye.

Exemplary chemical compounds, compositions or materials for enhancing detectability of luminescers include detergents such as, e.g., TRITON (manufactured by Rohm & Haas Co.), sodium deoxycholate, octylglucoside, sodium dodecylsulfate (SDS) and the like; enzymes such as phospholipase, esterases and phosphodiesterase; organic solvents, such as carbitol, dioxane and the like; mercaptans; sulfites; phosphites; hydroxyl amine; alkalis such as sodium hydroxide and the like. The above materials and their preparation or isolation are well-known in the art and many are commercially available.

Where the luminescer is adsorbed in a nonaqueous phase of a particle such as a liposome, a detergent is preferably selected as the reagent for enhancing the detectability of the luminescer. In those cases wherein the luminescer is associated with a particle by a covalent bond between the particle and the luminescer, a reagent that cleaves the bond between the luminescer and the particle can be employed for enhancing detectability of the luminescer. Where the bond is a disulfide bond a reagent such as a mercaptan, a sulfite, a phosphite, an alkali or the like is selected; esters are cleaved by utilizing an alkali, hydroxyl amine, esterases and the like; phosphates are cleaved by phosphodiesterases and the like; and acetals and orthoesters are cleaved by acids.

As mentioned above, the present invention involves a method of detecting luminescence as a measure of an analyte in a sample suspected of containing the analyte. The method permits optimal detection of a large number of luminescers that are reversibly associated with a nonaqueous phase of a particle conjugated to a member of a specific binding pair.

One aspect of the present invention involves a sensitive heterogeneous immunoassay which comprises combining in an assay medium (1) a sample suspected of containing an analyte, and (2) a composition that includes a conjugate of a first sbp member with a particle having a luminescer reversibly associated with a nonaqueous phase of the particle. In cases where the first sbp member is not complementary to the analyte, a second sbp member is included in the assay medium. The second sbp member is selected so that is is capable of binding to the analyte and to the first sbp member.

The present assay method has application to heterogeneous assays. Exemplary assays are found in U.S. Pat. Nos. 4,256,8834; and 4,261,968.

In carrying out the assay method of the present invention, a predetermined amount of the sample suspected of containing the analyte is measured. The amount of the sample chosen so as to result in an accurate and sensitive assay for the analyte will depend on the protocol selected. Because the present invention finds use in many protocols, one skilled in the art would understand that in general, the volume of the sample will range from about 25 to 100 $\mu$l, usually from about 50 to 100 $\mu$l. Depending on the sample and the initial volume, the sample can be diluted with an appropriate volume of distilled or deionized water or buffer.

In one approach, the sample suspected of containing the analyte of interest is combined in an assay medium with sbp bound particles having a luminescer reversibly associated with its nonaqueous phase. Subsequently, particles that have not bound to the analyte are separated from those that have bound. Separation may be accomplished by a variety of means, such as by adding a reagent, for example, an antibody that will coaggregate either the bound or the unbound fractions, or by contacting the suspension with a solid phase that will specifically bind either the bound or the unbound fractions, for example, by use of a second sbp member or an sbp member complementary with the analyte. Thereafter, a reagent is added to the unbound particles or to the bound particles to enhance the detectability of the luminescer and the luminescer is measured.

In another embodiment of the present invention involving a heterogenous immunoassay employing a solid support, a sample suspected of containing an analyte is combined in an assay medium with (1) a conjugate of a first sbp member and a fluorescer-containing liposome, wherein the fluorescer is dissolved in the nonaqueous phase of the liposome, and (2) a second sbp member that is bound to a support. The binding of the first sbp member to the second sbp member is affected by the concentration of the analyte in the sample. In such a method the support is separated from the assay medium and a reagent for enhancing the detectability of the fluorescer is added to the support or to the assay medium.

The selection of and the concentration of the reagent for enhancing detectability is generally dependent upon the nature of the association of the particle and the luminescer and the composition of the particles. Therefore, it is important to consider the characteristics of the particle and the nature of the association of the particle and the luminescer when choosing the reagent for reversing the association between the luminescer and the particle or otherwise enhancing the luminescence.

In general, the greater the quantity of the reagent used to reverse the association or otherwise enhance the signal, the faster will be the enhancement of the signal. To avoid any adverse effects on the assay there may be a need to limit the amount of the reagent. It will usually be desirable to utilize a concentration of the reagent that is sufficient to result in complete reversal of the association between the particles and the luminescer in less than 30 minutes, preferably in less than 10 minutes, more preferably in less than 1 minute.

When the selected particle is a polymer, e.g., a latex, relevant factors to be considered in selecting a reagent to enhance detectability include the nature of the association between the polymer and the luminescer. For example, in cases wherein the luminescer is dissolved in the polymer, a solvent should be chosen that will dissolve the particle in which the luminescer is dissolved. In cases wherein the luminescer is covalently attached to the surface of a polymer, a reagent should be selected that has the ability to cleave the bond between the luminescer and the particle.

When the selected particle is a liposome, relevant factors to be considered when selecting a reagent for enhancing detectability include selecting a reagent that will dissolve the liposome. Such reagents include detergents and the like. In cases wherein the luminescer is covalently bonded to the surface of the liposome, a reagent that will cleave the bond can be used.

The amount of the reagent for enhancing detectability of the luminescer employed will depend on various factors. These factors include, as suggested above, whether the reagent will dissolve the particulate material, in which case an amount of reagent sufficient to break up the particulate material, e.g., the liposome, is selected, or will cleave the bond between the particle and the luminescer, in which case an amount sufficient to cleave such bonds is chosen. Additionally, the concentration range of the analyte and the optimum volume for accurate liquid measurements and fluorometric determination and the like are taken into account. Such determinations are well within the ability of one skilled in the art.

The method of the present invention is utilizable in a wide range of protocols, therefore, the assay medium can contain additional members of a signal producing system, which can be present separate from or confined within the particles or both. The concentration of the various members of the signal producing system will vary and be dependent upon the concentration range of the analyte of interest.

Moderate temperatures are normally employed for carrying out an assay in accordance with the present invention and usually constant temperatures during the period for conducting the assay. Generally, the temperature for the assay will range from about 0° C. to 50° C., more usually from about 20° C. to about 40° C., most preferably at about 37° C. After the addition of a reagent for reversing the association between the particle and the luminescer or otherwise enhancing the detectability of the luminescer, a temperature that promotes the enhancement of the detectability of the luminescence is chosen. Again, moderate temperatures are generally employed and will usually range from about 0° C. to 50° C., more usually from about 20° C. to 40° C., and most preferably at ambient temperature.

In carrying out the method of the present invention the pH of the medium will be chosen so as to prevent reversal of the association between the particle and the luminescer, to control the stability of the reagents and to prevent unwanted reactions. Where the pH of the medium is not suitable for enhancing the detectability of the luminescer or for carrying out the assay, a suitable buffer will be added to the assay medium. Various buffers may be used to achieve the desired pH and to maintain the desired pH during the determination. The particular buffer employed is not critical to the invention, but in individual assays, one buffer may be preferred over another. Illustrative buffers include borate, phosphate, carbonate, Tris, barbital, and the like.

In addition to performing an assay for the analyte of interest, it will normally be desirable to perform assays with one or more calibrators, whereby one would obtain either a single value or a plurality of values at different concentrations and graph the concentration of the analyte versus the observed values to obtain a standard curve. No specific temperature control is required, as long as the calibrators and the analyte assay determinations are carried out under substantially similar conditions.

The invention will next be described in detail using a blood sample as exemplary of the assay sample and human Thyroid Stimulating Hormone (hTSH) as exemplary of the sbp member to be determined in accordance with the present method. This description is merely illustrative of the many assays in which the present method can be employed and is not meant to limit the scope of the present invention.

In carrying out an assay for hTSH utilizing the method of the present invention, a serum sample suspected of containing hTSH optionally in a buffered aqueous medium comprising greater than 5%, preferably greater than 20%, more preferably more than 50%, serum by volume is employed. The pH of the buffered aqueous medium is usually about 5 to 9, preferably 6 to 8. The sample is combined in an aqueous buffer with appropriate amounts of monoclonal antibody to the α-subunit of hTSH bound to biotin and fluorescent particles with monoclonal antibody to the β-subunit of hTSH bound thereto. The reagents can be premixed prior to their addition to the sample for the sake of convenience. The amount of reagents used is dependent on the suggested concentration of analyte in the sample, the binding affinities of the antibodies, and the like. Typically, about 0.1 μg to 100 μg, preferably 1 μg to 10 μg, of anti-hTSH to the α-subunit of hTSH bound to biotin are employed per ml of serum and 0.1 μg to 100 μg, preferably 1 μg to 5 μg of anti-hTSH to the β-subunit of hTSH bound to fluorescent particles are employed per ml of serum. The aqueous buffer containing the sample, the monoclonal antibody to the α-subunit of hTSH bound to biotin and the fluoresecent particle bound to the monoclonal antibody to the β-subunit of hTSH is incubated under conditions that will provide for the combination of the antibodies to hTSH with hTSH when that analyte is present in the serum. Incubation times may vary widely depending on the concentration of the analyte, the binding affinities of the antibodies, and the like. Desirable incubation times from the standpoint of convenience in conducting the assay are about 1 to 120 minutes, preferably five minutes to about 90 minutes, at mild temperatures usually about 10° C. to about 37° C.

Thereafter, the incubated mixture is combined with magnetic particles having avidin bound thereto in an aqueous solution. The amount of magnetic particles employed depends on the amount of antibody linked to biotin that is used in the assay. In a typical assay about 1 μg to 5 μg, preferably 1 μg to 2 μg, of avidin bound to magnetic particles can be employed per ml of biotin bound to antibody. The mixture is then incubated under conditions that will provide for combination of biotin and avidin. Desirable incubation times from the viewpoint of convenience of running an assay are about 5 minutes to 60 minutes, preferably about 5 minutes to about 30 minutes, at mild temperatures usually about 10° C. to about 37° C.

Subsequently, the magnetic particle-squarate dyed latex aggregate is separated by exposing the mixture to a magnetic field, for example by use of a bar magnet or use of a device such as a magnetic separator sold by Dow Corning Co. The liquid can be removed from the aggregate by decanting or aspiration or the like. The aggregate can then be resuspended using an aqueous buffer and again subjected to a magnetic field to ensure removal of contaminating material from the sample or occluded non-bound fluorescent label. The aggregate is resuspended in water and a reagent, such as a detergent, e.g., SDS, TRITON-X 100, and the like is added to reverse the association between the fluorescer and the particle.

After a period of about 45 seconds or more the fluorescence can be measured by use of a standard fluorometer. The medium is examined to determine any change in fluorescence as a result of the reversal of the association between fluorescer and the particle.

The present method has particular advantages in that luminescers associated with the nonaqueous phase of the particles are frequently more stable in the nonaqueous phase than in water. Additionally, a large quantity of the luminescer can be utilized without loss by breakage of vesicles or dissolution into the assay medium. As a result, compositions utilizable in the present invention have a long shelf life.

Luminescers that are used in the present invention are preferably dyes that are derivatives of 3,4-dihydroxy-3-cyclobutene-1,2-dione (squaric acid). Copending patent application Ser. No. 834,168, filed on Feb. 27, 1986 discloses squarate dyes.

In those cases wherein the particle selected is a carboxylate-modified polystyrene, it has been found that positively charged dyes, such as the rhodamine and carbocyanine or methine dyes do not penetrate sufficiently beyond the surface of the particles. Dyes which are zwitteronic and therefore electronically neutral, such as those that are derivatives of 3,4-dihydroxy-3-cyclobutene-1,2-dione, independently substituted with anilinyl or indoleninyl are preferable. Preferably, the dye chosen will be lipophilic particularly where the dye is dissolved in the lipid layer of a liposome or the like. Dyes that are symmetric are preferable, although non-symmetric dyes also work well.

In those cases wherein the particle itself is lipophilic, the squarate dye selected preferably mimics the lipophilic particle and has a lipophilic tail and a hydrophilic head.

It will be appreciated by those skilled in the art that those compounds that have a polar or polar groups such as hydroxl, amine, carboxy, sulfonic acid and the like will be hydrophilic or at least water compatible. Furthermore, it will be appreciated by those skilled in the art that those compounds that lack such polar groups will tend to be lipophilic in character.

The squarate dye employed in the present invention preferably incorporates one or more substituents that impart lipophilicity or hydrophobicity, such as, e.g., a hydrocarbon group having from 2 to 26 carbon atoms, preferably having at least 8 carbon atoms, or substituents that provide for enhanced affinity of the dye for a receptor. At least one functional group such as carboxy, hydroxy, sulfonic acid, amino, and the like are preferred where the dye is covalently bound to a nonaqeous phase of a particle.

For the most part the squarate dyes which can be utilized in the present invention will have the following formula

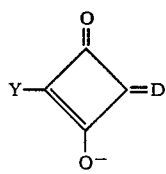

(I)

wherein:

D is independently selected from the group consisting of

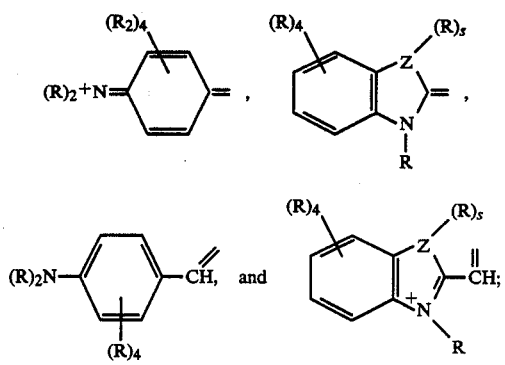

Y is independently selected from the group consisting of

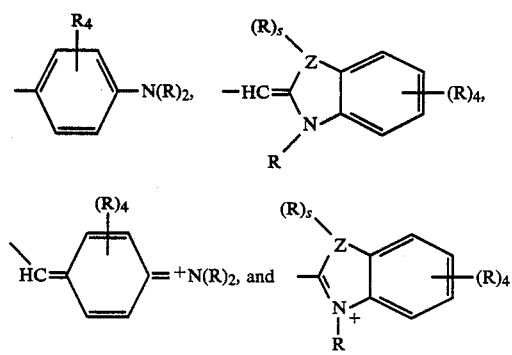

Z in D and Z in Y are independently selected from the group consisting of carbon, nitrogen, oxygen, sulfur, and selenium;

s is 2 when Z is carbon, 1 when Z is nitrogen, and O when Z is oxygen, sulfur, or selenium;

R is independently hydrogen or a substituent having from 1 to 56 atoms other than hydrogen, which atoms are selected from the group consisting of carbon, oxygen, nitrogen, sulfur, halogen of atomic number 9 to 53, boron with the proviso that, where D and Y are the same and all but one R group is lower alkyl (1 to 4 carbon atoms), the remaining R group has at least one heteroatom such as, for example, oxygen, nitrogen, or sulfur, or is a chain of at least five carbon atoms which may or may not have such heteroatom; R may be taken together with one or more other R groups to form one or more rings, usually five or six membered rings; R may contain one or more groups which are hydroxy, carboxy, including esters and amides thereof, sulfonic acid, amine including primary, secondary, and tertiary amine, aryl including phenyl, carbamate, succinimidyl and the like.

Preferred compounds are selected from the group consisting of

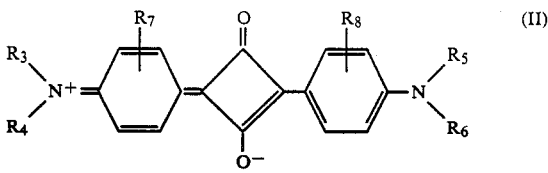

(II)

wherein:

$R_3$ and $R_4$ are independently selected from the group consisting of alkyl, alkenyl, and alkynyl groups of from 2 to 26, preferably 8 to 22 carbon atoms carbon atoms;

$R_5$ and $R_6$ are independently selected from the group consisting of hydroxyl, hydrogen, lower alkyl and carboxy substituted lower alkyl, including lower alkyl esters, wherein the lower alkyl has 1 to 10, preferably 1 to 5 carbon atoms; and $R_7$ and $R_8$ are independently selected from the group consisting of hydrogen, hydroxyl, methoxy, $R_3$ and $R_4$.

Particularly preferred compounds that can be utilized in the present invention have the above formula wherein $R_3$ and $R_4$ are independently selected from unsubstituted straight alkyl chains of from 8 to 22 carbon atoms; $R_5$ is lower alkyl with 1 to 5 carbon atoms; $R_6$ is carboxyl or carboxymethyl; and $R_7$ and $R_8$ are independently selected from hydrogen and hydroxyl.

The squarate dyes that can be utilized in the present invention can be prepared by a reaction sequence, the individual steps of which are separately known in the art. Some of the squarate dyes that can be utilized in the present invention can be made according to the procedures described by Sprenger et al., Angew. Chem., 80, 541 (1968); Springer et al., Angew. Chem., 79, 581 (1967); Sprenger et al., Angew. Chem. internat. Edit., 5, 894 (1966); and Maaks et al., Angew. Chem. internat. Edit., 5, 888 (1966).

In general, squaric acid (dihydroxycyclobutenedione) is condensed with an active compound such as a pyrrole, indolinine or an aniline. The condesation is conducted under conditions for removing water from the reaction mixture. For example, the condensation can be carried out under reflux in an alkanol/benzene solvent mixture. The resulting product can be collected and purified by, for example, recrystallization, distillation, chromatography, or the like. The group or functionality imparting lipophilic properties to the squarate dye that can be utilized in the present invention can be part of an initial reactant for the condensation or it can be introduced after the condensation by conventional techniques.

As a matter of convenience, the reagents for conducting an assay can be provided in a kit in package combination in predetermined amounts for use in assaying an analyte. The kit can comprise a luminescer that is reversibly associated with a nonaqueous phase of a particle conjugated to a member of a specific binding pair. The kit can also include a reagent for reversing the association of the luminescer with the nonaqueous phase of the particle. Furthermore, the kit can include ancillary agents as necessary.

EXAMPLES

The invention is demonstrated further by the following illustrative examples. All temperatures are in degrees Centigrade (°C.). Parts and percentages herein are by weight unless otherwise specified. The following abbreviations were used:

DMF - dimethylformamide
BGG - bovine gamma globulin
PBS - phosphate buffered saline (0.01 M sodium phosphate, 0.15 M NaCl, 0.005 M $NaN_3$, pH 7.0)
NHS - N-hydroxy succinimide
EDAC - 1-ethyl-3 (dimethylaminopropyl) carbodiimide hydrochloride
PBS/1% BGG - PBS containing 10 mgBGG/ml
BSA - bovine serum albumin
PGA - phospho-glucuronic acid
ANS - 8-anilino-1-naphthalene-sulfonic acid
THF - tetrahydrofuran
IHP - inositolhexophasphate

EXAMPLE 1

Preparation of N-hexadecyl-2,3,3-trimethylindolenium iodide 2,3,3-trimethylindolenine (4.78 grams) and 1-iodohexadecane (14 grams) were combined in 40 ml of benzene. The mixture was heated at reflux temperature for a period of seven days. The mixture was chromatographed on a silica gel column using 10% (v/v) methanol/methylene chloride and spots developed in an iodine chamber. The solvent was removed by rotary evaporation, and the oily residue was crystallized from a mixture of methanol and ethyl acetate. Crystals were collected by filtration and vacuum dried to give 9.18 grams of the product.

EXAMPLE 2

Preparation of bis-N-hexadecyl-2,3,3-trimethylindoleniumsquaraine

N-hexadecyl-2,3,3-trimethyl indolenium iodide (1.8 g) prepared as described in Example 1 and 3,4,-dihydroxy-3-cyclobutene-1,2-dione were combined in 30 ml of a mixture of butanol and benzene (2:1 v/v). The mixture was heated at reflux temperature for twenty hours and then evaporated to near dryness under vacuum. The residue was dissolved in chloroform and purified using ethyl acetate in hexane. The product containing eluate was evaporated to yield 1.06 grams of brilliant, irridescent green solid product. The absorption maxima in toluene is 644 nm.

EXAMPLE 3

Preparation of N,N-dihexadecylaniline

Aniline (0.93 g), 1-iodohexadecane (10.56 g) and diisopropylethylamine (2.58 g) were combined in 10 ml of toluene. The mixture was heated at about 100° C. for a period of three days. The mixture was chromatographed on a silica gel column using 1% ethyl acetate in hexane. The heavy crystalline mass that precipitated from solution was cooled, diluted with ether and filtered. The filtrate was concentrated to an oil and applied to a silica gel column. The oil was washed with 500 ml of hexane followed by 1% ethyl acetate in hexane. The dialkylated fractions were combined and evaporated to give 2.6 grams of product.

EXAMPLE 4

Preparation of bis-N,N-dihexadecylanilinium squaraine 3,4-dihydroxy-3-cyclobutene-1,2-dione (0.21 g) and N,N-dihexadecylaniline (2 g) prepared as described in Example 3 were combined in 50 ml of a mixture of butanol and benzene (1:2 v/v). The mixture was heated at reflux temperature for six hours. Thereafter 3,4-dihydroxy-3-cyclobutene-1,2-dione (0.1 g) was added and heating continued for an additional 6 hours. Benzene was allowed to boil away until upon cooling a thick slurry was formed. The product was filtered and a solid was recrystallized from propanol until the liquor was free of impurities. The product was washed with methanol and vacuum dried at 70° C. to give 1.18 grams of product as a waxy blue solid. The absorption maxima of the product in toluene is 637 nm.

EXAMPLE 5

Dyeing of Latex Beads

Five ml of benzyl alcohol were warmed at about 80° to 100° C.

Five mg of dye as prepared in Example 4 were dissolved in the heated benzyl alcohol. Fifteen milliliters of ethylene glycol were poured into a flask and equilibrated in an oil bath at 140° C. Ten ml (1 gram solids) of 0.716 $\mu$ diameter carboxylate-modified latex sold by Dow Chemical Co. were centrifuged, the pellets were resuspended in ethylene glycol (10 ml) and thereafter the bead suspension was added to the hot ethylene glycol and allowed to equilibrate. Small aliquots of the hot dye solution were slowly added below the surface to the vigourously stirring bead suspension. After all of the dye had been added, the mixture was stirred for about 7 minutes at 140° C. The flask was then removed from the oil bath and the contents were pipetted into 75 ml of 70% ethanol in water. The cooled suspension was centrifuged and the pellets were resuspended by sonication in 90% ethanol in water. The suspension was centrifuged at about 5000 rpm and the unincorporated free dye precipitate was separated from the beads. The beads were washed in water and resuspended in water (~100 mg/ml).

EXAMPLE 6

Preparation of N,N-dihexadecyl-m-aminophenol

Aminophenol (7.74 g), 1-iodohexadecane (50 g), ethyl diisopropyl amine (18.32 g) were combined in 25 ml of tetrahydrofuran. The mixture was stirred at reflux temperature for two days. The reaction liquor was decanted from the precipitated salts and the precipate was washed with ethyl ether. The liquor and the washes were combined and concentrated to an oil which was chromatographed on a silica gel column using 20% (v/v) ethyl acetate in hexane. The fractions containing the desired dialkylated product were combined and stripped to an oil that solidified to give 21 grams of the product.

EXAMPLE 7

Preparation of 3-(N-ethyl) aminophenol

A 1.0 M solution of borane-methyl sulfide in dichloromehtane (275 ml) was added dropwise to a solution of 3-acetamidophenol (161 g) in THF (800 ml) over about 1 to 2 hours. The mixture was heated to reflux temperature for about 4 hours and was then poured slowly into methanol (1 liter). The solvent was evaporated to a heavy syrup, which deposited crystals on cooling and scratching. The solid was collected by filtration and redissolved in methanol. Evaporation and recrystallization as above gave a 74% yield of the compound.

EXAMPLE 8

Preparation of 3-(N-ethyl-N-carbomethoxymethyl) aminophenol 3-(N-ethyl)aminophenol (18 g) as prepared in Example 7, methyl bromoacetate (20 g) and N,N-diisopropylethylamine (16.64 g) were combined and gently warmed. The reaction was allowed to proceed exothermically for about 1 to 2 hours. The mixture was diluted with methylene chloride (100 ml) after it reached ambient temperature, and thereafter was wahed with three portions of 0.1 N hydrochloric acid (100 ml), one portion of water (50 ml) and one portion of brine (50 ml). The methylene chloride solution was dried over anhydrous sodium sulfate and then evaporated to a viscous oil to give 21 grams of the product. The compound was checked for purity by thin liquid chromatography using 2% (v/v) methanol/methylene chloride and revealed a single spot.

EXAMPLE 9

Preparation of 1-[4-(dihexadecylamino)-2-hydroxyphenyl]-3-[4-(N-ethyl-N-carbomethoxymethylamino)-2-hydroxyphenyl]-2,4-dihyroxycyclobutenediylium dihydroxide, bis (inner salt)

A reaction vessel was charged with 13.3 g of the compound prepared in Example 6, 5 g of the compound prepared in Example 8, 2.72 g of squaric acid and 100 ml of n-butanol-benzene (1:2, v/v). The mixture was heated at reflux temperature for three hours. Upon cooling the reaction products precipitated to form a semi-solid mass that was then slurried in methanol and filtered. A portion of the reaction mixture was purified by preparative thin layer chromatography on silica gel plates, using 10% methanol in toluene as developing solvent. Elution of the desired band with a mixture of methanol//methylene chloride (1:2, v/v) followed by evaporation yielded 81 mg of the product.

EXAMPLE 10

Preparation of the Preferred Squaric Acid Methine Dye

Seventy-five mg of the compound prepared in Example 9 was dissolved in 30% dichloromethane in methanol and warmed with an excess of sodium hydroxide. Hydrochloric acid was added to the mixture and a violet precipitate was formed. The precipitate was collected, washed with methanol and dried. The compound was purified by thin layer chromatography on a silica gel plate, using methanol-toluene-acetic acid (10:90:1, v/v/v) as developing solvent.

EXAMPLE 11

Preparation of L-α(dioleoyl)-phosphatidyl ethanolamine 4-(N-maleimidomethyl)cyclohexone-1-carboxylate Succinimidyl 4-(N-maleimidomethyl) cyclohexane-1-carboxlate (SMCC) (17 mg) and triethylamine (7 μl) were added to a solution of dioleoylphosphatidyl ethanolamine (DOPE) (25 mg) in chloroform (2.5 ml). The mixture was sealed to prevent evaporation and was stirred at ambient temperature overnight. The reaction mixture was washed three times using 2 ml of 5% (v/v) methanol/water, and dried over anhydrous sodium sulfate. The mixture was chromatographed on a silica gel column using chloroform (5 ml), 5% (v/v) methanol/chloroform (5 ml), 10% (v/v) methanol/chloroform (5 ml) and 20% (v/v) methanol/chloroform as the developing solvent. Fractions containing product were combined and evaporated to give 28 mg of a white oily residue. By thin layer chromatography on silica gel, chloroform/methanol/acetic acid (60:20:3 v/v/v), the material was estimated to be greater than 95% pure.

EXAMPLE 12

Preparation of Maleimide Functionalized Membrane Dyed Phospholipid Vesicles

Palmitoyl oleoylphosphatidylcholine (POPC) (72 mg), palmitoyl oleoylphosphatidylglycerol (POPG) (8 mg), cholesterol (12 mg), L-α(dioleoyl)-phosphatidyl ethanolamine 4-(N-maleimidomethyl)cyclohexone-1-carboxylate (DOPE-MCC) (3 mg), and the product of Example 9 (1 mg) were combined in 5 to 10 ml of chloroform. The mixture was warmed gently and evaporated under a stream of nitrogen gas. The resulting oil was redissolved in chloroform (0.5 ml) and dried to a thin film on the walls of the vessel under a stream of nitrogen gas. Traces of solvent were removed under vacuum for 1 to 2 hours. The lipid film was then hydrated in four ml of 10 mM phosphate (pH 7). The lipid suspension had a deep blue color. The suspension was extruded through a series of progressively smaller membranes having a pore size of 2.0, 1.0, 0.8, 0.6 and 0.4 microns.

EXAMPLE 13

Preparation of Sulfhydryl Modified Antibody

To a solution of 10 mg of monoclonal antibody against human thyroid stimulating hormone (hTSH) in 3 ml of pH8.1 phosphate buffered saline at ambient temperature was added 50 molar equivalents of S-acetylmercaptosuccinic anhydride (SAMSA) (25 mM in DMF). After the reaction had proceeded at ambient temperature for one hour, the reaction mixture was then dialized twice against 500 ml of 0.1 M sodium phosphate/0.1 M sodium chloride/5 mM EDTA at ph7.5. Under an argon atmosphere the dializate (~3 ml) was reacted with 1 M hydroxylamine solution (0.3 ml) at pH7.5 for one hour at ambient temperature. Excess reagent was removed on a sephadex G-50 column (1×24 cm) equilibrated with 0.1 M sodium phosphate/0.1 M sodium chloride/5 mM EDTA at pH 6 under argon. Free sulfhydryl per antibody was determined with 5,5'-dithiobis (2-nitrobenzoic acid) (Ellman's reagent) and was found to be 6 per antibody.

EXAMPLE 14

Preparation of Antibody-Squarate Dyed Vesicle Conjugate 0.4 ml vesicles (8 mg phospholipid) prepared as described in Example 12 was added dropwise to 2 ml of sulfhydryl modified antibody (5.48 mg) prepared as described in Example 13. The vessel was capped under argon and the mixture was stirred at 4° C. for three days. The mixture was then passed through a sepharose 4B column (1.6×73 cm) equilibrated with 50 mM Tris /50 mM NaCl/0.05% NaN$_3$ at pH 8.5. The vesicles were eluted in the void volume and 1.86 mg of free antibody was recovered in the included volume.

EXAMPLE 15

Preparation of Maleimidated Aminodextran (MAD$_x$)

Sulfosuccinimidyl 4-(N-maleimidomethyl) cyclohexane-1-carboxylate (29.4 mg) was dissolved in water (1 ml) and immediately added at room temperature to a solution of aminodextran (100 mg, 75 µM free amine) dissolved in 6.65 ml of phosphate buffer at pH 7.5. After about 90 minutes the mixture was dialized three times with 2 liters of 10 mM sodium chloride to give the product.

EXAMPLE 16

Preparation of Sulfhydryl Modified Antibody

N-succinimidyl 3-(2-pyridyldithio) propionate (1.7 mg) was dissolved in 0.25 ml of ethanol and a 60 µl aliquot was added to PBS (10 ml, pH7.5) containing 33 mg of monoclonol antibody to the β subunit of hTSH. The reaction mixture was stirred for two hours at room temperature and then dialized twice against 1 liter of 0.1 M sodium phosphate (pH 7.5). Three ml of the dialyzate was further dialized against 1 liter of 50 mM sodium acetate (pH 4.5) and then made 25 mM in dithioerythritol. After 30 minutes at room temperature, the sulfhydryl modified antibody was separated from excess reagent using a sephadex G-50 column (1×24 cm) equilibrated with 10 mM sodium phosphate/50 mM sodium chloride/5 mM EDTA, 5 mM disodium EDTA, pH 7.5 under argon. Antibody containing fractions were pooled and sulfhydryl groups per antibody were determined by reaction with Ellman's reagent and found to be 4.

EXAMPLE 17

Preparation of MAD$_x$ Coated Latex

Squarate dyed carboxylate modified latex (50 mg) in water (1 ml) was mixed with EDAC (25 mg) in water (0.5 ml). After three minutes, the activated latex suspension was added to 6 ml of a solution containing MAD$_x$ (30 mg) in 10 mM sodium chloride. The mixture was sonicated to break up the aggregates. Excess reagents were removed by centrifugation and the coated latex was suspended in 10 mM sodium chloride solution.

EXAMPLE 18

Preparation of a Sulfhydryl Modified Antibody-MAD$_x$ Coated Latex Conjugate

MAD$_x$ coated latex (10 mg) as prepared in Example 17 was equilibrated in argon saturated PBS containing 1% by weight BGG and 1% by weight Tween 20. The suspension was sonicated briefly and then added to 4 ml of sulfhydryl modified antibody (5.24 mg) as prepared in Example 16. The mixture was briefly sonicated and then placed on a rotator at room temperature overnight. Excess antibody was removed with centrifuation to give the product.

EXAMPLE 19

Fluoroimmunoassay for hTSH with Squarate Dyed Latex Particles

The following assay was performed for hTSH using the method of the present invention. The following reagents were prepared and used in the assay.

Reagents:

Assay Buffer: 50 mM Tris-HCl/150 mM NaCl/0.1% BSA 0.05% Tween 20, pH 8.

Ab$_\alpha$: monoclonal antibody to α subunit of hTSH

Ab$_\alpha$-Biotin: ~10 biotin molecule/Abα; 1 µg Ab$_\alpha$/ml assay buffer

Ab$_\beta$: monoclonal antibody to β subunit of hTSH

Ab$_\beta$-FP: ~4×10$^9$ Squarate dyed latex particles/ml assay buffer, 0.2 micron diameter MP: PGA modified magnetizable particles MP-Avidin: MP coated with avidin by EDAC coupling, ~200 µg Fe, ~8 µg Avidin/ml assay buffer Releasing Agent: 5% SDS The protocol employed for carrying out an assay was as follows: 100 µl of hTSH was spiked into serum that was free of hTSH and mixed with 100 µl of Ab$_\alpha$-Biotin in assay buffer and 50 µl of Ab$_\beta$-FP in assay buffer and incubated for one hour at room temperature or 5 minutes at 37° C. Thereafter, 50 µl of sodium citrate in water (1.6 M) and 100 µl of MP-Avidin in PBS containing 1% by weight BSA was added to the mixture and incubated for about thirty minutes at room temperature or 5 minutes at 37° C. Subsequently, the magnetic particle-squarate dyed latex aggregate was separated using a magnetic separator (purchased from Dow Corning Company) and the supernatant was decanted. The aggregate was washed twice with about 1 ml of assay buffer. The aggregate was resuspended in water and about 0.5 ml of SDS was added. After about 45 seconds the fluorescence was measured using a fiber optic fluorometer (U.S. Pat. No. 4,564,598), using a He-Ne laser at 632.8 nm as the excitation source and measuring the emission.

Results of hTSH Assay with a combined incubation time of 10 minutes at 37° C. and a combined incubation time of one hour and thirty minutes at room temperature are summarized in Table 1 and Table 2, respectively.

TABLE 1

| hTSH (ng/ml) | Fluorescence Units (KHz) |
| --- | --- |
| 1.0 | 768 |
| 0.5 | 405 |
| 0.25 | 270 |
| 0.1 | 157 |
| 0 | 87 |

TABLE 2

| hTSH (ng/ml) | Fluorescence Units (KHz) |
| --- | --- |
| 1.0 | 355 |
| 0.1 | 110 |
| 0 | 78 |

The above results demonstrate that a rapid, accurate, sensitive assay for hTSH can be carried out in accordance with the teaching of the present invention. A substantial change in fluorescence was observed as the concentration of hTSH veried from 0, 0.1, 0.25. 0.5 to 1.0 ng/ml.

EXAMPLE 20

Fluoroimmunoassay for hTSH with Squarate Dyed Liposome Particles

The following assay was performed for hTSH using the method of the present invention. The following reagents were prepared and used in the assay.

Reagents:
Assay Buffer: 50 mM Tris-HCl/150 mM NaCl/0.1% BSA pH 8.
$Ab_\alpha$: monoclonal antibody to $\alpha$ subunit of hTSH
$Ab_\alpha$-Biotin: ~10 biotin molecule/$Ab_\alpha$; 1 $\mu$g $Ab_{60}$/ml assay buffer
$Ab_\beta$: monoclonal antibody to $\beta$ subunit of hTSH
$Ab_\beta$-FP: ~$4 \times 10^9$ Squarate dyed liposome particles/ml assay buffer, 0.2 micron diameter
MP: PGA modified magnetizable particles
MP-Avidin: MP coated with avidin by EDAC coupling, ~200 $\mu$g Fe, ~8 $\mu$g Avidin/ml assay buffer
Releasing Agent: Triton X-100

The protocol employed for carrying out an assay was as follows: 100 $\mu$l of hTSH was spiked into serum that was free of hTSH and mixed with 100 $\mu$l of $Ab_{60}$-Biotin in assay buffer and 50 $\mu$l of $Ab_{60}$-Biotin in assay buffer and 50 $\mu$l of $Ab_\beta$-FP in assay buffer and incubated for one hour at room temperature. Thereafter 50 $\mu$l of sodium citrate in water (1.6 M) and 100 $\mu$l of MP-Avidin in PBS containing 1% by weight BSA was added to the mixture and incubated for about 30 minutes at room temperature. Subsequently, the magnetic particle-squarate dyed liposome aggregate was separated using a magnetic separator (purchased from Dow Corning Company) and the supernatant was decanted. The aggregate was washed twice with about 1 ml of assay buffer. The aggregate was resuspended in water and about 0.5 ml of 0.25% Triton X-100 was added. After about 45 seconds the fluorescence was measured using a fiber optic fluorometer (U.S. Pat. No. 4,564,598), using a He-Ne laser at 632.8 nm as the excitation source and measuring the emission.

Results of hTSH Assay with a combined incubation time of 10 minutes at 37° C. and a combined incubation time of one hour and thirty minutes at room temperature are summarized in Table 3 and Table 4, respectively.

TABLE 3

| hTSH (ng/ml) | Fluorescence Units (KHz) |
|---|---|
| 1.0 | 244 |
| 0.5 | 157 |
| 0.2 | 94 |
| 0.1 | 84 |
| 0 | 62 |

TABLE 4

| hTSH (ng/ml) | Fluorescence Units (KHz) |
|---|---|
| 1.0 | 687 |
| 0.5 | 361 |
| 0.2 | 179 |
| 0.1 | 124 |
| 0 | 75 |

The above results demonstrate that a rapid, accurate, sensitive assay for TSH can be carried out in accordance with the teaching of the present invention. A substantial change in fluorescence was observed as the concentration of hTSH varied from 0, 0.1, 0.2, 0.5 to 1.0 ng/ml.

EXAMPLE 21

Fluoroimmunoassay for $T_3$ with Squarate Dyed Latex Particles

The following assay was performed for triiodothyronine ($T_3$) using the method of the present invention. The following reagents were prepared and used in the assay.

Reagents:
Assay Buffer: 0.075 M Na-barbital, 0.02% $NaN_3$, pH 8.6, 0.1% BSA
FP-$T_3$: Fluorescent latex particles labeled with BGG-$T_3$ conjugate by EDAC, ~$10^9$ particles per ml assay buffer, 0.2 $\mu$M diameter
Ab-Biotin: Polyclonal anti-$T_3$ antibodies, IgG fraction, biotinylated by biotin-NHS.
MP-Avidin: PGA modified magnetizable particles labeled with avidin by EDAC, ~37 to 40 $\mu$g avidin/mg of Fe.
Releasing Agent: 0.075 M Sodium-barbital, 1.9 mM ANS, 12.5 mM sodium salicylate, 0.02% $NaN_3$/pH 8.6
Ab Diluting Reagent: 0.0385 M sodium-barbital, 0.235 M sodium citrate, 0.1 M IHP, 4 mg/ml dextran-sulfate (MW 8000), 0.05% BSA, 0.02% $NaN_3$/pH 8.6
Ab Diluting Reagent: 0.0385 M sodium-barbital, 0.235 M sodium citrate, 0.1 M IHP, 4 mg/ml dextran-sulfate (MW 8000), 0.05% BSA, 0.02% $NaN_3$/pH 8.6
Washing buffer: 0.05 M Tris HCL/pH 8.0

The protocol employed for carrying out an assay was as follows: 500 $\mu$l of $T_3$ was spiked into serum that was free of $T_3$ and mixed with 100 $\mu$l of AB-Biotin in the antibody diluting solution and 50 $\mu$l of releasing agent and incubated for five hours at 37° C. Thereafter, 100 $\mu$l of FP-$T_3$ in assay buffer (1.6 M) was added to the mixture and incubated for 5 hours at 37° C. Then, 200 $\mu$l of MP-Avidin was added and incubated for 5 hours at 37° C. Subsequently, the magnetic particle-squarate dyed latex aggregate was separated using a magnetic separator (purchased from Dow Corning Company) and the supernatant was decanted. The aggregate was washed twice with about 1 ml of assay buffer. The aggregate was resuspended in water and about 0.5 ml of the releasing agent was added. After about 45 seconds the fluorescence was measured using a fiber optic fluorometer (U.S. Pat. No. 4,564,598), using a He-Ne laser at 632.8 nm as the excitation source and measuring the emission.

Results of $T_3$ Assay are summarized in Table 5.

TABLE 5

| $T_3$ (ng/ml) | Fluorescence Units (KHz) |
|---|---|
| 10.0 | 259 |
| 5.0 | 364 |
| 2.5 | 575 |
| 1.25 | 825 |
| 0.63 | 1046 |
| 0.31 | 1187 |
| 0 | 1311 |

The results dremonstrate that an accurate, sensitive assay for $T_3$ can be carried out in accordance with the teaching of the present invention. A substantial change in fluorescene was observed as the concentration of $T_3$ varied from 0, 0.31, 0.63, 1.25, 2.5 to 5.0 ng/ml.

Although the foregoing invention has been described in some detail by way of illustration and example for purposes of clarity and understanding, it will be obvious that certain changes or modifications may be practiced within the scope of the appended claims.

What is claimed is:

1. An assay method for determining an analyte in a sample suspected of containing said analyte wherein said analyte is a member of a specific binding pair (sbp) consisting of ligand and its complementary receptor, which method comprises the steps of
    (a) combining in an assay medium a sample suspected of containing an analyte and a conjugate of a first sbp member with a particle wherein said particle is selected from the group consisting of liposomes, latex particles and cells and wherein a fluorescer is reversibly associated with a nonaqueous phase of said particle by dissolving said fluorescer in said nonaqueous phase of said particle; with the proviso that when said first sbp member is not complementary to said analyte, a second sbp member capable of binding to the analyte and said first sbp member is added;
    (b) separating the unbound conjugate from conjugate that is bound to said analyte or said sbp member;
    (c) adding to said bound conjugate or said unbound conjugate a reagent for reversing the association of said fluorescer;
    (d) after reversing the association of said fluorescer by the addition of said reagent, exposing said fluorescer to a light source at a wavelength which causes excitation of said fluorescer;
    (e) measuring the light emission of said fluorescer acted upon by said light source; and
    (f) relating the measured light emission to the amount of analyte in said sample.

2. The method according to claim 1 wherein said fluorescer is selected from the group consisting of squarate dyes, umbelliferones, fluoresceins, cyanines, merocyanines, and rhodamines.

3. The method according to claim 1 wherein said fluorescer when associated with said particle is incapable of producing a signal.

4. The method according to claim 1 wherein said reagent is a detergent or an organic solvent that is capable of reversing the association of said fluorescer by partial or complete dissolution of said particle.

5. The method according to claim 1 wherein said sbp members are members of an immunological pair consisting of antigen and antibody.

6. The method according to claim 1 wherein said analyte is selected from the group consisting of antigens, haptens and antibodies.

7. The method of claim 1 wherein said analyte is selected from the group consisting of drugs, proteins, polypeptides, nucleic acids and polysaccharides.

8. The method according to claim 7 wherein said drugs are selected from the group consisting of theophylline, thyroxine and digoxin.

9. The method according to claim 1 wherein said particle is a liposome which is a phospholipid vesicle.

10. The method according to claim 1 wherein said unbound conjugate is separated from said conjugate by contacting said assay medium with a surface having bound to it an sbp member complementary with said analyte or said second sbp member.

11. The method according to claim 1 wherein said assay medium is contacted with magnetizable particles which bind to the bound conjugate and the bound conjugate is separated from the unbound conjugate by exposing the sample to a magnetic field.

12. The method according to claim 1 wherein said first sbp member is antibody and said particle is a liposome.

13. The method according to claim 1 wherein said first member is antigen and said particle is a liposome.

14. A method according to claim 22 wherein said squarate dye is a compound of the formula:

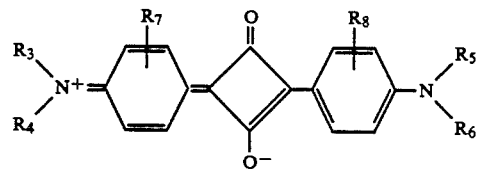

wherein $R_3$ and $R_4$ are independently selected from the group consisting of alkyl, alkenyl, and alkynyl groups of from 2 to 26 carbon atoms;

$R_5$ and $R_6$ are independently selected from the group consisting of lower alkyl and hydroxyl substituted and carboxy substituted lower alkyl, including lower alkyl esters, wherein the lower alkyl has 1 to 10 carbon atoms; and $R_7$ and $R_8$ are independently selected from the group consisting of hydrogen, hydroxyl, methoxy, $R_3$ and $R_4$.

15. The method according to claim 1 wherein said second sbp member is bound to a solid support.

16. The method according to claim 1 wherein said conjugate either bound or unbound to analyte is separated from said medium by binding to a solid support.

17. The method according to claim 15 wherein said support is selected from the group consisting of immunochemical strips, microtiter plate wells, magnetic particles, latex beads and glass beads.

18. An assay method for determining an analyte in a sample suspected of containing said analyte wherein said analyte is a member of a specific binding pair (sbp) consisting of ligand and its complementary receptor, which method comprises the steps of
    (a) combining in assay medium (1) a sample suspected of containing an analyte; (2) a conjugate of a first sbp member and a fluorescer-containing liposome wherein said fluorescer is reversibly associated with the nonaqueous phase of said liposome by dissolving said fluorescer in said nonaqueous phase of said liposome; and (3) a second sbp member bound to a support and which can bind conjugates either bound or unbound to the analyte; wherein the extent of binding between said bound and unbound conjugate and said second sbp member is affected by the concentration of said analyte in said sample;
    (b) separating the support from said medium;
    (c) adding to said support or said medium a reagent for reversing association of said fluorescer with said liposome;
    (d) after reversing the association of said fluorescer by the addition of said reagent, exposing said fluorescer to a light source at a wavelength which causes excitation of said fluorescer;
    (e) measuring the light emission of said fluorescer acted upon by said light source; and
    (f) relating the measured light emission to the amount of analyte in said sample.

19. The method according to claim 18 wherein said fluorescer is selected from the group consisting of squarate dyes, umbelliferones, fluoresceins, cyanines, merocyanines and rhodamines.

20. The method according to claim 18 wherein said fluorescer is a squarate dye having an absorption maximum greater then 600 nm.

21. The method according to claim 18 wherein said sbp members are members of an immunological pair consisting of antigen and antibody.

22. The method according to claim 18 wherein said analyte is selected from the group consisting of antigens, haptens and antibodies.

23. The method of claim 18 wherein said analyte is selected from the group consisting of drugs, proteins, nucleic acids and polysaccharides.

24. The method according to claim 23 wherein said drugs are selected from the group consisting of theophylline, thyroxine and digoxin.

25. The method according to claim 18 wherein said liposome is a phospholipid vesicle.

26. The method according to claim 18 wherein said reagent is a detergent or an organic solvent that is capable of reversing the association of said fluorescer by partial or complete dissolution of said liposome.

27. The method according to claim 18 wherein said fluorescer is a squarate dye, said second sbp member is antibody and said liposome is a phospholipid vesicle.

28. The method according to claim 18 wherein said fluorescer is a squarate dye, said first sbp member is antibody and said liposome is a phospholipid vesicle.

29. A method according to claim 20 wherein said squarate dye is a compound of the formula:

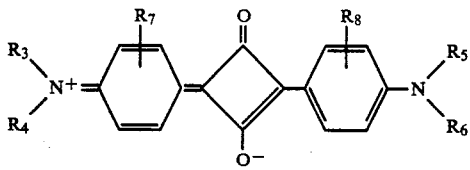

wherein $R_3$ and $R_4$ are independently selected from the group consisting of alkyl, alkenyl, and alkynyl groups of from 2 to 26 carbon atoms;

$R_5$ and $R_6$ are independently selected from the group consisting of lower alkyl and carboxy substituted and hydroxyl substituted lower alkyl, including lower alkyl esters, wherein the lower alkyl has 1 to 10 carbon atoms; and $R_7$ and $R_8$ are independently selected from the group consisting of hydrogen, hydroxyl, methoxy, $R_3$ and $R_4$.

30. The method according to claim 18 wherein said support is selected from the group consisting of immunochemical strips, microtiter plate wells, magnetic particles, latex beads and glass beads.

31. An assay method for determining an analyte in a sample suspected of containing the analyte wherein the analyte is a member of a specific binding pair (sbp) consisting of ligand and its complementary receptor, which method comprises the steps of (a) combining in an assay medium a sample suspected of containing an analyte and a conjugate of a first sbp member and a fluorescer-containing particle wherein said particle is selected from the group consisting of liposomes, latex particles and cells and wherein said fluorescer is reversibly dissolved in a nonaqueous phase of said particle; with the proviso that when said first sbp member is not complementary to said analyte, a second sbp member capable of binding to the analyte and said first sbp member is added;

(b) separating the unbound conjugate from conjugate that is bound to said analyte or said second sbp member;

(c) adding to said bound conjugate or said unbound conjugate a reagent for reversing said dissolution;

(d) after addition of said reagent, exposing said fluorescer to a light source at a wavelength which causes excitation of said fluorescer;

(e) measuring the light emission of said fluorescer released from said bound conjugate or said unbound conjugate acted upon by said light source; and (f) relating the measured light emission to the amount of said analyte in said sample.

32. The method according to claim 31 wherein said fluorescer is selected from the group consisting of squarate dyes, umbelliferones, fluoresceins, cyanines, merocyanines, and rhodamines.

33. The method according to claim 31 wherein said reagent for reversing the confinement of said fluorescer is selected from the group consisting of detergents and organic solvents.

34. The method according to claim 31 wherein said unbound conjugate is separated from said bound conjugate by contacting said assay medium with a surface having bound to it an sbp member complementary with said analyte or said second sbp member.

35. The method according to claim 31 wherein said first sbp member is an antigen and said particle is a liposome.

36. An assay method for determining an analyte in a sample suspected of containing said analyte wherein said analyte is a member of a specific binding pair (sbp) consisting of ligand and its complementary receptor, which method comprises the steps of (a) combining in an assay medium (1) a sample suspected of containing an analyte; (2) a conjugate of a first sbp member and a liposome having a squarate dye dissolved in the nonaqueous phase of said liposome; and (3) a second spb member bound to a support and which can bind conjugates either bound or unbound to the analyte; wherein the amount of binding between said bound or unbound conjugates and said second sbp member is in relation to the concentration of said analyte in said sample;

(b) separating said support from said medium;

(c) combining said support or said medium with a reagent selected from a group consisting of (1) an aqueous solution of a detergent and (2) an organic solvent;

(d) after the combination of said reagent with said support or said medium, exposing the system to a light source at a wavelength which causes excitation of the squarate dye;

(e) measuring the light emission of the squarate dye; and (f) relating the measured light emission to the amount of said analyte in said sample.

37. The method according to claim 36 wherein said squarate dye has an absorption maximum greater than 600 nm.

38. The method according to claim 36 wherein said first and second sbp members are members of an immunological pair consisting of antigen and antibody.

39. The method according to claim 36 wherein said analyte is selected from the group consisting of antigens, haptens and antibodies.

40. The method of claim 36 wherein said analyte is selected from the group consisting of drugs, proteins, nucleic acids and polysaccharides.

41. The method according to claim 40 wherein said drugs are selected from the group consisting of theophylline, thyroxine and digoxin.

42. The method according to claim 36 wherein said liposome is a phospholipid vesicle.

43. The method according to claim 36 wherein in step (c) said support is combined with an aqueous solution of a detergent.

44. The method according to claim 36 wherein said first sbp member is antibody.

45. The method according to claim 36 wherein said first sbp member is antigen.

46. A method according to claim 36 wherein said squarate dye is a compound of the formula:

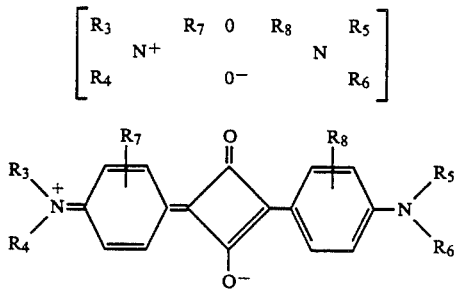

wherein $R_3$ and $R_4$ are independently selected from the group consisting of alkyl, alkenyl, and alkynyl groups of from 2 to 26 carbon atoms;

$R_5$ and $R_6$ are independently selected from the group consisting of hydroxyl, hydrogen, lower alkyl and carboxy substituted lower alkyl, including lower alkyl esters, wherein the lower alkyl has 1 to 10 carbon atoms; and $R_7$ and $R_8$ are independently selected from the group consisting of hydrogen, hydroxyl, methoxy, $R_3$ and $R_4$.

47. A kit for use in an assay for an analyte that is a member of a specific binding pair (sbp) consisting of ligand and its complementary receptor comprising in a packaged combination:

(a) a conjugate of a first sbp member and a squarate dye containing particle wherein said particle is selected from the group consisting of liposomes, latex particles and cells and further wherein said squarate dye is reversibly associated with a nonaqueous phase of said particle by dissolving said squarate dye in said nonaqueous phase of said particle; with the proviso that when said first sbp member is not complementary to said analyte, a second sbp member capable of binding to the analyte and said first sbp member is also contained in the kit;

(b) a reagent for reversing the association of said squarate dye with said non-aqueous phase of said particle.

48. The kit according to claim 47 wherein said reagent is selected from detergents and organic solvents.

49. An assay method for determining an analyte in a sample suspected of containing said analyte wherein said analyte is a member of a specific binding pair (sbp) consisting of ligand and its complementary receptor, which method comprises the steps of (a) combining in an assay medium a sample suspected of containing an analyte and a conjugate of a first sbp member with a liposome wherein a squarate dye having an absorption maximum greater than 600 nm is reversibly dissolved in the nonaqueous phase of said liposome; with the proviso that when said first sbp member is not complementary to said analyte, a second sbp member capable of binding to the analyte and said first sbp member is added;

(b) separating the unbound conjugate from conjugate that is bound to said analyte or said second sbp member;

(c) adding to said bound conjugate or said unbound conjugate a reagent for reversing the dissolution of said squarate dye;

(d) after reversing the dissolution of said squarate dye by the addition of said reagent, exposing the system to a light source at a wavelength which causes excitation of the squarate dye;

(e) measuring the light emission of said squarate dye acted upon by said light source; and (f) relating the measured light emission to the amount of said analyte in said sample.

50. The method according to claim 49 wherein the reagent is a detergent or an organic solvent that is capable of reversing the association of said squarate dye by partial or complete dissolution of said liposome.

51. The method according to claim 49 wherein said sbp members are members of an immunological pair consisting of antigen and antibody.

52. The method according to claim 49 wherein said analyte is selected from the group consisting of antigens, haptens and antibodies.

53. The method according to claim 49 wherein said analyte is selected from the group consisting of drugs, proteins, nucleic acids and polysaccharides.

54. The method according to claim 49 wherein said liposome is a phospholipid vesicle.

55. The method according to claim 49 wherein said unbound conjugate is separated from said bound conjugate by contacting said assay medium with a surface having bound to it an sbp member complementary with said analyte or said second sbp member.

56. The method according to claim 49 wherein said assay medium is contacted with magnetizable particles which bind to the bound conjugate and the bound conjugate is separated from the unbound conjugate by exposing the sample to a magnetic field.

* * * * *

UNITED STATES PATENT AND TRADEMARK OFFICE
CERTIFICATE OF CORRECTION

PATENT NO. : 4,891,324
DATED : January 2, 1990
INVENTOR(S) : John Pease, Litai Weng, Hrair Kirakossian, Edwin f. Ulman Page 1 of 1

It is certified that error appears in the above-identified patent and that said Letters Patent is hereby corrected as shown below:

<u>Column 23,</u>
Line 9, "75 µM" should read -- 58 µm --.

Signed and Sealed this

Eleventh Day of September, 2001

Attest:

*Nicholas P. Godici*

NICHOLAS P. GODICI
*Acting Director of the United States Patent and Trademark Office*

*Attesting Officer*